(12) United States Patent
Von Eichelstreiber et al.

(10) Patent No.: US 9,066,961 B2
(45) Date of Patent: Jun. 30, 2015

(54) MEDICAMENT FOR LCT POISONING

(75) Inventors: Christoph Von Eichelstreiber, Schweppenhausen (DE); Jessica Reineke, Bad Schwalbach (DE); Stefan Tenzer, Mainz (DE); Hansjoerg Schild, Schwabenheim (DE); Maja Rupnik, Limbus (SI)

(73) Assignee: JOHANNES GUTENBERG-UNIVERSITAET MAINZ, Mainz (DE)

(*) Notice: Subject to any disclaimer, the term of this patent is extended or adjusted under 35 U.S.C. 154(b) by 0 days.

(21) Appl. No.: 13/483,701

(22) Filed: May 30, 2012

(65) Prior Publication Data

US 2013/0280286 A1    Oct. 24, 2013

Related U.S. Application Data

(63) Continuation of application No. 12/376,036, filed as application No. PCT/DE2007/000957 on May 26, 2007, now abandoned.

(30) Foreign Application Priority Data

Aug. 2, 2006  (DE) .......................... 10 2006 036 373
Jan. 26, 2007  (DE) .......................... 10 2007 004 938

(51) Int. Cl.
  *A61K 31/56*      (2006.01)
  *A61K 31/6615*    (2006.01)
  *A61K 31/04*      (2006.01)
  (Continued)

(52) U.S. Cl.
  CPC ............. *A61K 31/6615* (2013.01); *A61K 31/04* (2013.01); *A61K 31/661* (2013.01); *A61K 39/08* (2013.01); *A61K 2039/505* (2013.01); *C07K 16/1282* (2013.01); *C07K 2316/96* (2013.01);
  (Continued)

(58) Field of Classification Search
  CPC ....................................................... A61K 31/56
  USPC ............................................................. 424/1
  See application file for complete search history.

(56) References Cited

U.S. PATENT DOCUMENTS 4,929,438 A * 5/1990 Sawai et al. ................... 514/143
5,736,139 A   4/1998 Kink et al.
(Continued)

FOREIGN PATENT DOCUMENTS

EP    0341810    * 11/1989
WO    88/070470   *  9/1988 ............. C07F 9/177
(Continued)

OTHER PUBLICATIONS

Xu, Yong et al, Tetrahedron Letters, vol. 46, pp. 8311-8314, 2005, Synthesis of phosphatase-resistant analogues of phytic acid (InsP6).*
(Continued)

*Primary Examiner* — Albert Navarro
*Assistant Examiner* — Ginny Portner
(74) *Attorney, Agent, or Firm* — Joyce von Natzmer; Agris & von Natzmer LLP (57) ABSTRACT

The medicament for the prevention or the relief of poisoning by large clostridial cytotoxins (LCTs), in particular *Clostridium difficile* toxins A and B (TcdA and TcdB), is characterized by containing as active ingredient at least one effector, namely an inhibitor or activator of the autocatalytic protease activity of LCTs (large clostridial cytotoxins).

10 Claims, 6 Drawing Sheets

(51) Int. Cl.

| | | |
|---|---|---|
| A61K 31/661 | (2006.01) | |
| A61K 39/08 | (2006.01) | |
| C07K 16/12 | (2006.01) | |
| A61K 31/336 | (2006.01) | |
| C07K 14/33 | (2006.01) | |
| C07K 16/40 | (2006.01) | |
| C12N 9/99 | (2006.01) | |
| A61K 39/00 | (2006.01) | |

(52) U.S. Cl.
CPC .............. *A61K 31/336* (2013.01); *C07K 14/33* (2013.01); *C07K 16/40* (2013.01); *C12N 9/99* (2013.01)

(56) References Cited

U.S. PATENT DOCUMENTS

| | | | | |
|---|---|---|---|---|
| 5,977,078 | A * | 11/1999 | Traynor-Kaplan et al. | 514/23 |
| 6,245,803 | B1 * | 6/2001 | Acosta et al. | 514/440 |
| 6,415,234 | B1 * | 7/2002 | Andre et al. | 702/27 |
| 6,733,760 | B1 | 5/2004 | Wilkins et al. | |
| 8,110,551 | B2 * | 2/2012 | Shenker et al. | 514/21.2 |
| 8,257,946 | B2 * | 9/2012 | Satchell | 435/69.1 |
| 8,546,523 | B2 * | 10/2013 | Osterkamp et al. | 530/300 |
| 8,557,548 | B2 * | 10/2013 | Anderson et al. | 435/71.3 |
| 2002/0012671 | A1 * | 1/2002 | Hildreth et al. | 424/208.1 |
| 2004/0208944 | A1 * | 10/2004 | Malnoe et al. | 424/764 |
| 2005/0203006 | A1 * | 9/2005 | Hill et al. | 514/9 |
| 2005/0287150 | A1 | 12/2005 | Ambrosino et al. | |
| 2006/0018931 | A1 * | 1/2006 | Taylor | 424/239.1 |
| 2006/0093592 | A1 * | 5/2006 | Cheruvanky et al. | 424/93.45 |
| 2006/0147476 | A1 * | 7/2006 | Schofield | 424/268.1 |
| 2006/0211619 | A1 * | 9/2006 | Steward et al. | 514/12 |
| 2008/0003329 | A1 * | 1/2008 | Rueda et al. | 426/72 |
| 2009/0130225 | A1 * | 5/2009 | Chakrabarti et al. | 424/617 |
| 2009/0170790 | A1 * | 7/2009 | Das et al. | 514/28 |
| 2009/0311258 | A1 * | 12/2009 | Von Eichelstreiber et al. | 424/139.1 |
| 2010/0256094 | A1 * | 10/2010 | Nicolau et al. | 514/77 |
| 2011/0218176 | A1 * | 9/2011 | Jennings-Spring | 514/102 |
| 2011/0243991 | A1 * | 10/2011 | Reineke | 424/239.1 |
| 2012/0258936 | A1 * | 10/2012 | Savidge et al. | 514/143 |
| 2013/0005690 | A1 * | 1/2013 | Savidge et al. | 514/103 |
| 2013/0012687 | A1 * | 1/2013 | Bogyo et al. | 530/350 |
| 2014/0045799 | A1 * | 2/2014 | Savidge et al. | 514/143 |
| 2014/0235590 | A1 * | 8/2014 | Castagner et al. | 514/102 |

FOREIGN PATENT DOCUMENTS

| | | | |
|---|---|---|---|
| WO | 99/24461 | A1 | 5/1999 |
| WO | 2005/058353 | A1 | 6/2005 |

OTHER PUBLICATIONS

Florin et al, Biochimica et Biophysica Acta, vol. 805, 1984, pp. 131-136, Polyphosphate medicated protection from cellular intoxication with *Clostridium difficile* toxin B.*

Pruitt, Rory N. et al, Journal of Biological Chemistry, vol. 284(33), Aug. 14, 2009, Structure-Function Analysis of Inositol Hexakisphosphate-induced Autoprocessing in *Clostridium difficile* Toxin A, pp. 21934-21940.*

Martin, Loic; Cornille, Fabrice; Turcaud, Serge; Meudal, Hervé; Roques, Bernard P. & Fournié-Zaluski, Marie-Claude, 1998: "Metallopeptidase Inhibitors of Tetanus Toxin: A Combinatorial Approach", in: J. Med. Chem. 42, pp. 515-525.

Chrzanowska, J.; Kolaczkowska, M.; Dryja'Nski M.; Stachowiak, D. & Polanowski, A., 1995: "Aspartic proteinase from *Penicillium camemberti*: Purification, properties, and substrate specificity", in: Enzyme and Microbial Technology 17: 719-724.

Claudiu T. Supuran et al: "Bacterial protease inhibitors", in: Medicinal Research Reviews, vol. 22, No. 4, Jun. 6, 2002, pp. 329-372.

Rode K et al: "The presence of manganese and potassium activates the *Clostridium difficile* Toxin B." in Naunyn-Schmiedeberg's Archives of Pharmacology, vol. 367, No. Supplement 1, Mar. 2003, pp. R54.

Faruki H et al: "Effect of calcium on in-vitro activity of LY-146032 against *Clostridium-difficile*," in Antimicrobial Agents and Chemotherapy, vol. 31, No. 3, 1987, pp. 461-462.

Reineke Jessica et al: "Autocatalytic cleavage of *Clostridium difficile* toxin B." in Nature Mar. 22, 2007, vol. 446, No. 7134, Mar. 22, 2007, pp. 415-419.

Rupnik et al., "Characterization of the cleavage site and function of resulting cleavage fragments after limited proteolysis of *Clostridium difficile* toxin B (TcdB) by host cells," in Microbiology, vol. 151, 2005, pp. 199-208.

Moos et al., "Purification and evaluation of large clostridial cytotoxins that inhibit small GTPases of Rho and Ras subfamilies," in Methods in Enzymology, vol. 325, pp. 114-125.

Pfeifer et al., "Cellular uptake of *Clostridium difficile* Toxin B," in J. Biol. Chem., vol. 278, No. 45, Nov. 7, 2003, pp. 44535-44541.

Rao et al., "Molecular and biotechnological aspects of microbial proteases," in Microbiol. Mol. Biol. Rev., vol. 62, No. 3, Sep. 1998, pp. 597-635.

Salto et al., "In vitro characterization of nonpeptide irreversible inhibitors of HIV proteases," in J. Biol. Chem., vol. 269, No. 14, Apr. 8, 1994, pp. 10691-10698.

Tang, "Specific and irreversible inactivation of pepsin by substrate-like epoxides," in J. Biol. Chem., vol. 246, No. 14, Jul. 25, 1971, pp. 4510-4517.

Egerer et al., "Auto-catalytic cleavage of *Clostridium difficile* toxins A and B depends on cysteine protease activity," in J. Biol. Chem., vol. 282 (35), Aug. 31, 2007, pp. 25314-21. Epub Jun. 25, 2007.

* cited by examiner

SEQUENCE LISTING

<160> NUMBER OF SEQ ID NOS: 4

<210> SEQ ID NO 1
<211> LENGTH: 26
<212> TYPE: PRT
<213> ORGANISM: Clostridium difficile
<220> FEATURE:

-continued

```
<221> NAME/KEY: MISC_FEATURE
<222> LOCATION: (1653)..(1678)
<223> OTHER INFORMATION: Catalytic center of the protease function of
      TcdB

<400> SEQUENCE: 1

Gln Asn Met Ile Val Glu Pro Asn Tyr Asp Leu Asp Asp Ser Gly Asp
1               5                   10                  15

Ile Ser Ser Thr Val Ile Asn Phe Ser Gln
            20                  25

<210> SEQ ID NO 2
<211> LENGTH: 25
<212> TYPE: PRT
<213> ORGANISM: Clostridium difficile
<220> FEATURE:
<221> NAME/KEY: MISC_FEATURE
<222> LOCATION: (1651)..(1675)
<223> OTHER INFORMATION: Catalytic center of the protease function of
      TcdA

<400> SEQUENCE: 2

Arg Asn Val Val Val Glu Pro Ile Tyr Asn Pro Asp Thr Gly Glu Asp
1               5                   10                  15

Ile Ser Thr Ser Leu Asp Phe Ser Tyr
            20                  25

<210> SEQ ID NO 3
<211> LENGTH: 26
<212> TYPE: PRT
<213> ORGANISM: Clostridium sordellii
<220> FEATURE:
<221> NAME/KEY: MISC_FEATURE
<222> LOCATION: (1654)..(1679)
<223> OTHER INFORMATION: Catalytic center of the protease function of
      TcsL

<400> SEQUENCE: 3

Gln Asn Leu Ile Val Glu Pro Ser Tyr His Leu Asp Asp Ser Gly Asn
1               5                   10                  15

Ile Ser Ser Thr Val Ile Asn Phe Ser Gln
            20                  25

<210> SEQ ID NO 4
<211> LENGTH: 25
<212> TYPE: PRT
<213> ORGANISM: Clostridium novyi
<220> FEATURE:
<221> NAME/KEY: MISC_FEATURE
<222> LOCATION: (1641)..(1663)
<223> OTHER INFORMATION: Catalytic center of the protease function of
      Tcn-alpha

<400> SEQUENCE: 4

Cys Asn Val Ile Val Ser Gly Ser Asn Lys Leu Asn Ser Glu Gly Asp
1               5                   10                  15

Leu Ala Asp Thr Ile Asp Val Leu Asp
            20                  25
```

MEDICAMENT FOR LCT POISONING

CROSS-REFERENCE TO RELATED APPLICATIONS

This is a continuation of U.S. patent application Ser. No. 12/376,036, which is the U.S. national stage of International application PCT/DE2007/000957, filed May 26, 2007 designating the United States and claiming priority to German applications. DE 102006036373.6, filed Aug. 2, 2006 and DE 102007004938.4, filed Jan. 26, 2007.

FIELD OF THE INVENTION

The invention relates to a medicament for the prevention or the relief of poisoning by large clostridial cytotoxins (LCTs), in particular *Clostridium difficile* Toxins A and B (TcdA and TcdB), *Clostridium sordellii* lethal Toxin (TcsL) and *Clostridium novyi* α-Toxin (Tcnα).

BACKGROUND OF THE INVENTION AND INTRODUCTION OF THE INVENTION

*Clostridium difficile* is a gram-positive, spore-forming germ, growing strictly anaerobically, which was only identified at the end of the 1970s as an etiological agent of antibiotic-associated diarrhoea and pseudomembranous colitis. Since the 1990s, *C. difficile* has been regarded as the most significant hospital germ in developed countries. As a consequence of the continuously expanding use of broad spectrum antibiotics, the incidence of *C. difficile* infections is constantly increasing further especially in people treated as in-patients.

The exotoxins toxin A (TcdA) and toxin B (TcdB) produced by *C. difficile* are responsible for the *C. difficile*-associated diseases. Various strains exist with different virulence and toxin production. Approximately one quarter of all strains produces no toxins. Toxin-forming strains produce almost always both toxins. TcdA is an enterotoxin which through cytotoxic damage to the enterocytes increases the permeability of the intestinal mucosa and hence initiates diarrhoea. TcdB is a cytotoxin which disturbs the electrolyte transportation and is responsible for loss of fluid and functional disturbances of the intestine. The toxins TcdA and TcdB belong to the group of so-called large clostridial cytoxins (LCTs) and consist respectively of a peptide chain with three functional domains, namely the C-terminal domain, which is responsible for binding the toxin to the host cell membrane, the hydrophobic middle domain, which is made (co)responsible for the translocation process through the cellular membranes, and the N-terminal domain, which has a glycosyltransferase function and imparts the toxic activity of the molecule.

The uptake process of the toxins in the host cell is in fact not yet fully explained, however it is considered a fact that the toxins, after binding to a host cell receptor, arrive into the host cell by endocytosis, and that for the development of their toxicity the N-terminal catalytic domain is split off and is conveyed into the cytosol of the host cell. There, the catalytic domain glycolizes specifically GTPases of the Rho sub-family (Rho, Rac and Cdc42), which in turn are involved in an abundance of signal transduction cascades, and in this way blocks the respective signal transduction processes, which finally leads to the disaggregation of the cytoskeleton and to cell death.

In the prior art, hitherto it was assumed that the splitting off of the catalytic N-terminal domain of the toxin peptide chains of TcdA and TcdB and also other "large clostridial toxins" LCT being catalyzed by a cellular protease (Rupnik et al., 2005 and Pfeiffer et al., 2003). Corresponding evidence was not, however, able to be provided.

In the course of the investigations which form the basis of the present invention, it was now surprisingly found, however, that the cleavage of TcdA and TcdB is an autocatalytic process, which is initiated by inositol phosphate (IP), and that consequently the toxins of *Clostridium difficile*, in addition to their catalytic function of glycosyltransferase also have the function of a protease for auto-cleavage or autocatalytic cleavage.

This protease function was identified as aspartate protease. As catalytic centre of the protease function, the protein region was identified which comprises the amino acid sequence of amino acid position AS 1653 to AS 1678 of TcdB according to sequence No. P18177 (SwissProt/TrEMBL). The motif DXG (Rao et al. 1998) characteristic for aspartate proteases lies at the amino acid position 1665.

As inositol phosphate binding site, the protein region was identified which comprises the amino acid sequence of amino acid position AS 1517 to AS 2142 of the TcdB protein according to sequence No. P18177 (SwissProt/TrEMBL). This amino acid sequence constitutes an inosin-5-monophosphate-dehydrogenase (IMPDH) motif, which is composed of two regions, namely AS 1517-AS 1593 and AS 1918-AS 2142, which are separated by a 325 amino acid long protein section without sequence homology.

For the treatment of patients with *C. difficile* infections, firstly the initiating antibiotic is discontinued, in so far as this is possible. The further treatment takes place exclusively symptomatically. With a long-lasting or serious etiopathology, and when a discontinuance of the initiating antibiotic is not possible for other reasons, metrondiazol or vancomycin is administered for therapy.

The disadvantages of the current antimicrobial therapy are manifold. It is critical here above all that a disease which was initiated as a result of the treatment of a different infection situation with antibiotics can not be effectively healed with an antimicrobial therapy. The background to this is the fact that *C. difficile* only occurs relatively rarely in the gut of healthy people and can not stand up to the normal intestinal flora. If the normal intestinal flora is destroyed by antiobiotic therapy, *C. difficile* can establish itself and can effectively colonize the gut. The antibiotic therapy directed against *C. difficile* leads in turn to the destruction of the intestinal flora and thereby causatively also prevents the development of a healthy intestinal flora. This also explains the large number of remissions which are to be observed after completion of the antimicrobial therapy. An additional disadvantage of the current therapy is the increasing occurrence of multiresistant *C. difficile* strains in recent times. The threat thereby is that the sole therapy hitherto for diseases induced by *C. difficile* also will become useless and the number of deaths as a result of *C. difficile* diseases will increase. In addition to this is the fact that the antibiotics necessary for the treatment of a *C. difficile* infection are very expensive and normally are only used in justified cases as reserve antibiotics.

SUMMARY OF THE INVENTION

There is therefore an urgent need for medicaments which are suited for the specific combatting (prevention, elimination, relief) of *C. difficile* infections, without the risk existing of the development of resistances in the clostridia or also other bacteria, and without damaging the natural bacteria flora of the patient concerned—in particular his intestinal flora.

An object of the present invention is the provision of such a medicament.

A solution to the said problem consists in the provision of a medicament of the type mentioned in the introduction, which is distinguished in that it contains as active ingredient at least one effector, namely an inhibitor or an activator of the autocatalytic protease activity of LCTs (large clostridial cytotoxins), in particular of the autocatalytic protease activity of *Clostridium difficile* toxin A (TcdA) and/or *Clostridium difficile* toxin B (TcdB) and/or *Clostridium sordellii* lethal toxin (TcsL) and/or *Clostridium novyi* α-toxin (Tcnα).

Both activators and also inhibitors of the autocatalytic protease activity of LCTs are designated below as effectors of the autocatalytic protease activity of LCTs.

If the active ingredient or effector is an inhibitor, then its antitoxic effect is based on the fact that it inhibits the protease activity of the intact toxin, in particular of the TcdB or TcdA or TcsL or Tcnα, and thereby prevents the splitting off of the cytotoxically effective fragment with glucosyltransferase function (in the case of TcdB and TcdA that is the 63 kDa fragment).

Suitable inhibitors are chemical substances which inhibit the protease activity of the toxins.

The term "chemical substance" in the above and following explanations designates both inorganic and also organic compounds, ions and peptides or proteins.

Preferred inhibitors are those chemical substances which inhibit the protease activity irreversibly. An example of this is the substance EPNP (1,2-epoxy-3-(p-nitrophenoxy)-propane). The substance reacts irreversibly with aspartate residues in the catalytic centre of proteases and thus inhibits the proteolytic effect.

Further protease inhibitors are known to the specialist in the art or can be easily identified by him by known methods (computer modelling, high throughput screening). For example, to carry out a high throughput screening, a peptide can be synthesized, the amino acid sequence of which corresponds to the sequence of the protease cleavage site of the LCTs. By coupling this peptide for example with the dye AMC (7-amino-4-methyl-cumarin) by methods which are known to the specialist in the art, a probe can be generated. To carry out the high throughput screenings, the labelled probe is then brought together with the toxin and the candidate substances. If the probe is split, then changes occur in the fluorescence spectrum. These changes are easy to detect by methods with which the specialist in the art is familiar (fluorescence detectors). Batches in which no change to the fluorescence spectrum are to be observed then contain potential protease inhibitors.

By way of example, a further method is described for the identification of substances which influence the activation of the autocatalytic protease activity of the PCTs. For this, the holotoxin or also suitable toxin fragments can be used, which for example are coupled with a dye, the fluorescence of which is quenched in the non-split toxin or toxin fragment. Through the autocatalytic cleavage of the toxin or of the toxin fragments, the quenching effect is removed. The changes in the fluorescence spectrum can be easily detected, as described.

Particularly suitable inhibitors, i.e. effectors with inhibitor function are chemical substances, in particular proteins and, amongst these especially antibodies, which inhibit the autocatalytic protease activity of the LCTs by interacting with the active centre of the protease.

The term "interact" in the present context means any kind of reciprocal action between the LCTs and a chemical substance, in particular a protein, and comprises in particular covalent bonds such as for example disulphide bonds and non-covalent bonds, such as for example van der Waals forces, hydrophobic or electrostatic reciprocal actions and hydrogen bridge bonds.

Proteins are preferred here, and amongst these especially antibodies which interact with the TcdB protein region of AS 1500 to AS 1800, in particular from AS 1653 to AS 1678 and especially with the DXG motif at position 1665—respectively according to TcdB amino acid sequence No. P18177 (SwissProt/TrEMBL) or the protein regions equivalent or homologous thereto of TcfA or TcsL or Tcnα. These equivalent/homologous protein regions are, in the case of TcdA, the amino acid sequence section of AS 1651 to AS 1675 according to TcdA amino acid sequence No. P16154 (SwissProt/TrEMBL) with the DXG motif at amino acid position AS 1662, in the case of TcsL, the amino acid sequence section of AS 1654 to AS 1679 according to TcsL amino acid sequence No. Q46342 (SwissProt/TrEMBL) with the DXG motif at amino acid position AS 1666, and in the case of Tcnα, the amino acid sequence section of AS 1641 to AS 1665 according to Tcnα amino acid sequence No. Q46149 (SwissProt/TrEMBL).

Further suitable inhibitors (effectors with inhibitor functions) are chemical substances, in particular proteins and, amongst these especially antibodies, which inhibit the autocatalytic protease activity of the LCTs, by inhibiting the interaction of the inositol phosphate with the toxin. By the IP bond being prevented, the proteolytic cleavage of the toxins does not occur.

Proteins are preferred here, and amongst these especially antibodies which interact with the TcdB protein regions of AS 1400 to AS 2300, in particular of AS 1517 to AS 2142 and especially of AS 1517 to AS 1593 or AS 1918 to AS 2142—respectively according to TcdB amino acid sequence No. P18177 (SwissProt/TrEMBL)—or with the protein regions, equivalent or homologous hereto, of the toxins TcdA or TcsL or Tcnα. Equally well, antibodies or other proteins can also be generated, which do not interact directly with the inositol phosphate binding site, in particular with the above-mentioned protein regions, but rather are directed towards adjacent regions and hinder the IP binding sterically and hence prevent the proteolytic cleavage of the toxins. Furthermore, antibodies or other proteins can be generated, which do not interact directly with the DXG motif of the protease function of the LCTs, but rather prevent the proteolytic cleavage by binding in adjacent protein sections.

Suitable inhibitors (effectors with inhibitor function) are constituted in addition by structural analogues of inositol phosphate (IP) and in particular of inositol hexaphosphate (IP6), which instead of IP and in particular of IP6 can occupy the reaction binding sites of LCT, in particular TcdA and/or TcdB, and/or TcsL and/or Tcnα, but do not have the initiator function of IP or IP6. These structural analogues are therefore antagonists to the agonists IP (in particular IP6) and bring about a competitive inhibition of the protease activity of LCT, in particular of TcdA and/or TcdB and/or TcsL and/or Tcnα. Suitable structural analogues are known to the specialist in the art or can be easily identified by known test methods with which the specialist in the art is familiar (examples of these have already been described above).

Suitable inhibitors are, in addition, inhibiting substances for/of inositol phosphate (synonyms: inositol phosphate inhibiting substance or inositol phosphate inhibitor), i.e. those inhibiting substances which bind or modify inositol phosphate and in particular inositol hexaphosphate such that its capability of initiating the protease activity of LCT, in particular of TcdA and/or TcdB and/or TcsL and/or Tcnα is prevented. An example of such substances are bivalent ions such as $Ca^{2+}$, which enter into insoluble complexes with IP6. Similar substances are known to the specialist in the art or can be easily identified by test methods which are known and with which the specialist in the art is familiar (examples of these are already described above).

Further suitable inhibitors (effectors with inhibitor function) are chemical substances which suppress the formation of inositol phosphates in the gut lumen of the patients (mammals, especially humans) or in the body cells of the patients (mammals, especially humans) or destroy already present inositol phosphate and thus prevent the proteolytic cleavage of the LCTs on penetration into the cytoplasm. Preferred examples of such substances are lithium, VPA (valproic acid) or CBZ (carbamazepine).

Suitable activators, i.e. effectors with activator function, are chemical substances which activate the protease activity of the toxins.

The antitoxic effect of an activator is based on the fact that it initiates the protease activity of the intact toxin, in particular of the TcdB or TcdA or TcsL or Tcnα, still before the toxin has bonded to the host cell such that the split off fragment could arrive into the cell interior (cytosol). The activator consequently brings about a splitting off of the cytotoxically effective fragment with glucosyl transferase function (in the case of TcdB and TcdA, that is the 63 kDa fragment) outside the host cell. The cytotoxically effective fragment can then no longer arrive into the cell interior and develop its cytotoxic effect there.

A particularly suitable activator (effector with activator function) is isolated (in contrast to cytosolic) inositol phosphate (IP), preferably inositol hexaphosphate (IP6).

A medicament with this active ingredient has the advantage that LCT present in the patient's gut, in particular TcdB and/or TcdA and/or TcsL and/or Tcnα is already caused to cleave in the gut through the IP supplied as medicament, i.e. before it can bind to gut cells or other body cells and act toxically.

Equally suited as activator (effector with activator function) is a substance which, in an analogous manner to IP6, promotes the autocatalytic protease activity of LCT, in particular of TcdA and/or TcdB and/or TcsL and/or Tcnα.

Such substances are known to the specialist in the art or can be easily identified by known methods. In addition, modified variants of the "high throughput assays" described above are also suitable for this. Here, the toxin and the potential activator substances are added together and in the course of time, changes in the fluorescence spectrum are sought. Batches in which intensive changes occur in a short period of time contain suitable activators (effectors with activator function).

The catalytic centres of the protease function of the LCTs can also be used according to the invention as systematically administered antigens (vaccination substances) to produce an immunisation against the toxins. The subject of the present invention is therefore also a medicament for the prevention or the relief of poisoning by LCT (=large clostridial cytotoxins), which is characterized in that it is suitable for administration as a vaccine, and that it has the amino acid sequence of the catalytic centre of TcdB and/or TcdA and/or TcsL and/or Tcnα, wholly or fragments thereof as antigen active ingredient(s). The antigen active ingredient(s) is/are preferably selected from the following group of protein fragments:

DXG motif at position 1665 of the TcdB amino acid sequence No. P18177 (SwissProt/TrEMBL),
the amino acid positions AS 1653 to AS 1678 of the TcdB amino acid sequence No. P18177 (SwissProt/TrEMBL),
the amino acid positions AS 1500 to AS 1800 of the TcdB amino acid sequence No. P18177 (SwissProt/TrEMBL),
the DXG motif at position 1662 of the TcdA amino acid sequence No. P16154 (SwissProt/TrEMBL),
the amino acid positions AS 1651 to AS 1675 of the TcdA amino acid sequence No. P16154 (SwissProt/TrEMBL)
the DXG motif at position 1666 of the TcsL amino acid sequence No. Q46342 (SwissProt/TrEMBL)
the amino acid positions AS 1654 bis AS 1679 of the TcsL amino acid sequence No. Q46342 (SwissProt/TrEMBL),
the amino acid positions AS 1641 to AS 1665 of the Tcnα amino acid sequence No. Q46149 (SwissProt/TrEMBL).

BRIEF DESCRIPTION OF THE FIGURES

The invention is described in further detail below with the aid of example embodiments and figures, showing.

DESCRIPTION OF VARIOUS AND PREFERRED EMBODIMENTS

All the methods named in the following examples are known to the specialist in the art and are described for example in Ausubel et al. (2003).

Example 1

Evidence of the Autocatalytic Protease Activity of TcdB

*Clostridium difficile* toxin B (270 kDa) of the reference strain VPI10463, abbreviated below to $TcdB_{10463}$, was initially fluoresence-marked with Cy3.

For this, 200-400 μg $TcdB_{10463}$ (tgcBIOMICS, Mainz, Germany) were marked with the dye Cy3 in accordance with the instructions of the manufacturer (Amersham Biosciences), by the toxin being incubated with the dye, dissolved in diemethyl formamide, for 1 hour at 4° C. Non-bonded dye was then removed by means of size exclusion chromatography (=SEC), in which 10 mM Tris-HCl pH 8.5 served as run buffer. The molar ratio between dye and Cy3-marked $TcdB_{10463}$ was 0.8-1.6. Marked $TcdB_{10463}$ was aliquoted and stored at −80° C. until further use.

(A) To carry out the "In-vitro-cleavage-assay" known from the prior art (see in this respect in particular Rupnik et al (2005); reference is hereby made expressly to the content of this publication) an aliquot Cy3-marked $TcdB_{10463}$, thawed to room temperature, was incubated for 1 hour at room temperature with pig spleen cell extract.

This pig spleen cell extract was produced as follows: Freshly obtained pig spleen was held in phosphate buffer (PBS) and comminuted to a single cell suspension. Through the addition of low salt buffer,—namely 150 mM $NH_4Cl$, 1 mM $KHCO_3$, 0.1 mM EDTA, pH 7.6-, erythrocytes which were present were lysed and thereby removed. Then the spleen cells were washed twice with 10 mM Tris-HCl pH 8.5 and deep-frozen immediately at −80° C. For the desired cell extract, as required an aliquot of these deep-frozen spleen cells was thawed in an aliquot 10 mM Tris-HCl pH 8.5 and suspended and this suspension was then subjected to an ultrasonic treatment. The obtained lysate was centrifuged for 1 hour at 200 000×g and 4° C. and the supernate was used for the upcoming experiments.

At the end of the incubation phase, the mixture of Cy3-marked $TcdB_{10463}$ and pig spleen extract was subjected to a SDS-PAGE, in order to separate and detect the TcdB fragments which occurred during the incubation. The result of this SDS-PAGE is illustrated in FIG. 1*a*: As expected, the two known and characteristic 63 kDa and 207 kDa fragments of the *Clostridium difficile* Toxin B—here the $TcdB_{10463}$—were obtained.

Aliquots of $TcdB_{10463}$ without admixture of spleen cell extract served as negative controls (see FIG. 1 "−").

(B) In a parallel experiment, the spleen cell extract described in (A) was purified of protein before the incubation with the Cy3-marked $TcdB_{10463}$. For this purpose, an aliquot of the pig spleen extract produced according to (A) was subjected to six phenol-chloroform extractions, following the ultrasonic treatment, which extractions were carried out as follows: Pig spleen extract was mixed with phenol-chloroform-isoamyl alcohol (25/24/1) in the volume ratio 1:1. This mixture was centrifuged for 10 minutes at 1,7000×g and 4° C. The aqueous uppermost layer was decanted into a fresh centrifuge vessel and centrifuging and decanting was repeated for a further five times. In order to also remove final residues of phenol, finally a chloroform extraction was carried out.

Aliquots of the aqueous and protein-free fraction of the spleen cell extract obtained in this way were diluted in the volume ratio 1:30 (30), 1:100 (100) or 1:300 (300) with 10 mM tris-HCL pH8.5 and, as described under (A), mixed with aliquots of Cy3-marked $TcdB_{10463}$, thawed to room temperature, and incubated for 1 hour at room temperature. At the end of the incubation phase, these mixtures were subjected to a SDS-PAGE, in order to separate and detect the TcdB fragments which occurred during the incubation. The result of this SDS-PAGE was made visible by means of the Gel Doc EQ system image readers (BIO-RAD Munich, Germany) and is illustrated in FIG. 1*b*: In all test batches the two characteristic 63 kDa and 207 kDa fragments of $TcdB_{10463}$ were obtained. This shows that the aqueous and protein-free fraction of the spleen cell extract still has or had the characteristic of splitting $TcdB_{10463}$ into its two characteristic partial fragments.

In a further parallel experiment, the spleen cell extract described in (A) was treated with heat (96° C., 30 minutes), before it was incubated as described in (A) with Cy3-marked $TcdB_{10463}$ and was subjected to the SDS-PAGE. The result of this SDS-PAGE is likewise illustrated in FIG. 1*b*. Again, the two characteristic 63 kDa and 207 kDa fragments of $TcdB_{10463}$ were obtained.

The result shows that the heat-induced spleen cell extract continues to have the characteristic of splitting $TcdB_{10463}$ into its characteristic partial fragments.

(C) In a further series of experiments, Cy3-marked $TedB_{10463}$ and unmarked $TcdB_{10463}$ were incubated alone (i.e. without the admixture of spleen cell extract) with various inositol phosphates for 1 hour at room temperature and the respective mixtures were then subjected to a SDS-PAGE. The result of these investigations is illustrated in Table 1 and in FIGS. 1*c-e* and provide the surprising core conclusions, that the proteolytic cleavage of $TcdB_{10463}$ is able to be initiated solely through a chemical substance such as IP, and that this proteolytic cleavage is consequently an autocatalytic process of the toxin protein.

From Table 1, it can be seen that a range of inositol phosphates can initiate the autocatalytic cleavage of $TcdB_{10463}$. Inositol hexaphosphate ($IP_6$) brings about the strongest cleavage activity amongst the tested inositol phosphates, and this means $W_6$ has the highest initiator activity (see also FIG. 1*c-e*).

Structural analogues or other substances related to the inositol phosphates, which have an initiator activity, are known to the specialist in the art or can be easily determined by known methods (e.g. computer modelling). For example, the "High Throughput Assays" described above can also be used.

The testing out of different concentrations of $IP_6$ in the incubation experiment with $TcdB_{10463}$ shows (see FIGS. 1*c* and 1*d*) that for the cleavage of fluorescence-marked toxin B, an IP concentration of 10 μM (FIG. 1*c*) is sufficient, whereas for the cleavage of unmarked toxin B (and only made visible in the SDS-PAGE by zinc stain (Zinc Stain and Destain Kit, Biorad, Hercules, USA)), still lower concentrations of up to 1 μm (FIG. 1 *d*) are sufficient.

Analogous experiments were also carried out with the LCTs $TcdA_{10463}$, TcsL of *C. sordellii* and Tcnα. Here it was found that inositol phosphates have an activating effect on the autocatalytic cleavage of all investigated toxins of the LCT family.

(D) In order to rule out that the $TcdB_{10463}$, purified from culture supernate of *C. difficile*, used in the experiments, was contaminated with proteases, a control experiment with especially purified $TcdB_{10463}$ was carried out. This purification of the $TcdB_{10463}$ took place by means of affinity chromatography with the use of the monoclonal antibody 2CV (DSM ACC 2321) as follows:

7 mg of the TcdB specific monoclonal antibody 2CV (ProteinG-purified supernate of a serum-free hybridoma culture) was coupled to a HiTrap NHS sepharose column (commercially available at GE Healthcare, Freiburg, Federal Republic of Germany). Coupling and elution were carried out according to the instructions of the manufacturer. The finished column was charged with approximately 4 mg $TcbB_{10463}$ and non-bonded proteins were removed by washing three times with 50 mM tris/HCl, pH 7.0; 125 mM NaCl. The elution took place in one step with 0.1 M triethanolamine-HCl pH11. The toxin eluted in three 4 ml fractions with concentrations between 450-185 µg/ml. The eluted toxin was immediately neutralized with 1M tris-HCl pH 7.5 in the volume ratio 1/10, which was guaranteed in that these neutralizing solution had already been provided before the start of the elution in the collecting tubes for the fractions. The absence of contaminating proteins was then demonstrated by SDS-PAGE and subsequent zinc stain (see FIG. 1 $e$ "–").

Figure 1:
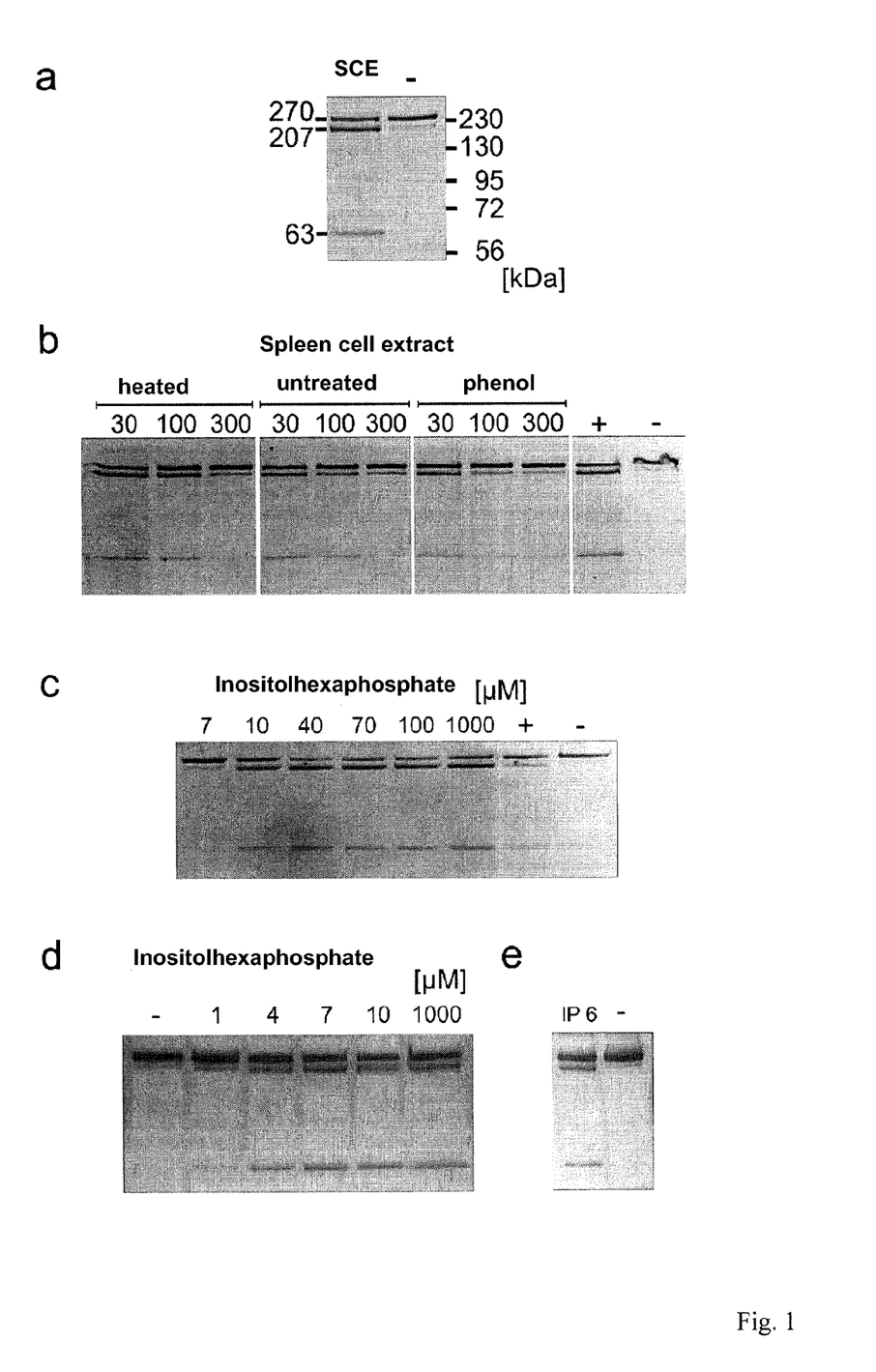
FIG. 1: Cleavage of the $TcdB_{10463}$ (270 kDa) holotoxin into the translocation/ligand domain (207 kDa) and the N-terminal catalytic domain (63 kDa) in SDS-PAGE, carried out with
a: a mixture of Cy3-marked $TcdB_{10463}$ and pig spleen cell extract (Example 1A);
b: a mixture of Cy3-marked $TcdB_{10463}$ and pig spleen cell extract freed of protein (Example 1B);
c: a mixture of Cy3-marked $TcdB_{10463}$, and inositol phosphate;
d: a mixture of unmarked $TcdB_{10463}$ and inositol phosphate;
e: a mixture of unmarked (purified by means of affinity chromatography) $TcdB_{10463}$ and inositol phosphate;
a-e respectively following an incubation at room temperature for 1 hour

The control experiment consisted of the incubation of unmarked $TcdB_{10463}$, purified in such a way, with $IP_6$, and subsequent SDS-PAGE and demonstration of the toxin or of the toxin fragments by means of zinc stain. The result of this experiment is illustrated in FIG. 1e and shows the complete cleavage of the holotoxin into the two known fragments 63 kDa and 207 kDa.

Example 2

Inactivation of TcdB-10463 Through Incubation with a Protease Inhibitor $TcdB_{10463}$ was purified as described in Example 1 (D) by means of affinity chromatography with the use of the monoclonal antibody 2CV and then pre-treated either (i) with the protease inhibitor EPNP (10 mM 1,2-epoxy-3-(p-nitrophenoxy)-propane) or (ii)—as control—with buffer (50 mM HEPES, 1M NaCl, 1 mM EDTA, pH 8.0) for 60 minutes at room temperature.

Then an in vitro cleavage assay analogous to Example 1 (A) was carried out. The test batches comprised respectively a volume of 10 µl, and contained respectively 50-100 ng unmarked $TcdB_{10463}$, 100 µM IP6 and 10 mM tris-HCl pH 8.5. Following the incubation (1 h at room temperature), these test batches were subjected to a SDS-PAGE (10%) and the toxins and toxin fragments were then made visible by means of zinc stain.

Figure 2:
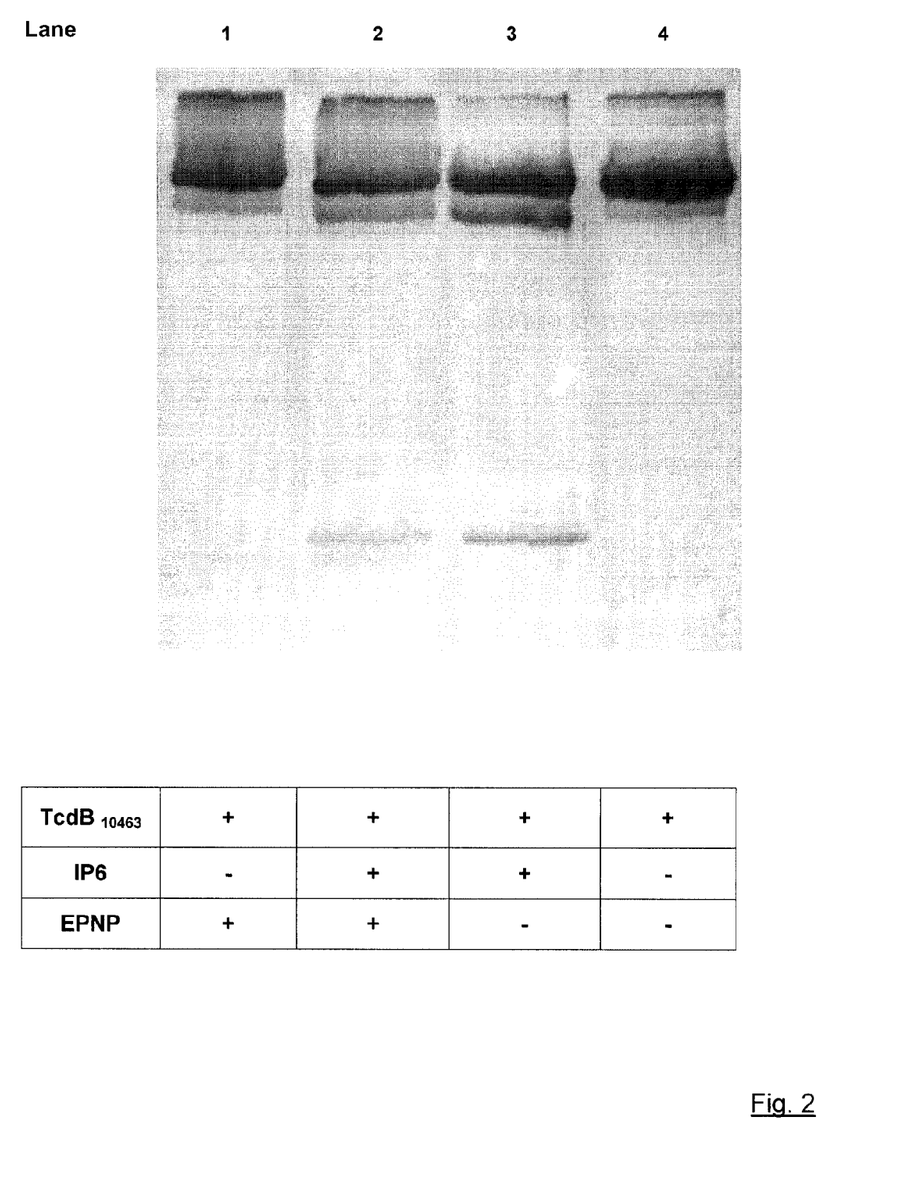
FIG. 2: SDS-PAGE of a mixture of $TcdB_{10463}$ and/or IP6, with or without pre-treatment of the toxin with EPNP;
Line 1: $TcdB_{10463}$ after pre-treatment with EPNP and without IP6, no band able to be evidenced in the 63 kDa range;
Line 2: $TcdB_{10463}$ after pre-treatment with EPNP and after incubation with IP6, the typical 63 kD band is only weakly formed;
Line 3: $TcdB_{10463}$ without pre-treatment with EPNP and after incubation with IP6, a distinctly formed band can be seen in the molecular weight range of 63 kDa;
Line 4: $TcdB_{10463}$ without pre-treatment with EPNP and without IP6, no band is able to be evidenced in the 63 kDa range.

FIG. 2 shows the result of this experiment: The incubation of $TcdB_{10463}$ alone with IP6 (Line 3) shows a distinctly marked band in the molecular weight range of 63 kDa. When the toxin is previously pre-treated with EPNP (Line 2), the typical 63 kD band is only weakly marked. This finding shows that through the addition of EPNP, the proteolytic activity (protease activity) of the $TcdB_{10463}$ is almost completely inhibited.

The toxin pre-treated with EPNP was additionally investigated in the CHO test according to Moos et al. (2000) for its residual activity (cytotoxic effect).

The CHO test was carried out as follows: In a 96 well microtiter plate, CHO cells (=Chinese hamster ovarial cells) were disseminated (5000 cells/well) and incubated for 16 hours under standard conditions (5% $CO_2$, DMEM F12 supplemented with 2 mN L-glutamins, 5% FCS). The toxins were then introduced to the cells after gradual dilution in growth medium. Dilution stages between $10^0$ and $10^{-8}$ were tested. The cells were incubated for 3 hours under standard conditions. Then the proportion of rounded cells was determined microscopically, by several representative sections of the well being photographed and the elongated and the rounded cells being counted. (See also Moos et al., Meth Enzymol. 2000, 325: 114-125. Reference is made here expressly to the content of this publication).

The results of this CHO test show that the $TcdB_{10463}$ pre-treated with EPNP has a substantially weaker cytotoxic effect than the untreated $TcdB_{10463}$ (cf. Table 2). As the inhibiting effect of EPNP, as is known, is based on the fact that EPNP enters into covalent interactions with catalytic aspartate residues and thereby brings about an irreversible inactivation of the protease (Salto et al. 1994), the results of the present experiment show that the inhibiting of the $TcdB_{10463}$ activity is based on the inhibiting of a protease activity of this toxin molecule.

The experiment with EPNP described here proves that the toxic effect of TcdB-$_{0463}$ and other LCTs is significantly reduced by pre-treatment of the toxins with a suitable protease inhibitor.

EPNP constitutes a model substance for a covalent inhibitor of the LCTs. Further comparably covalently-acting or competitively-inhibiting inhibitors are known to the specialist in the art or can be determined by him by known methods, for example by the already described "high throughput assays".

Example 3

Inactivation of the Cytotoxic Effect of $TcdB_{10463}$ Through Extracellular Activation of the Protease Activity with IP6

$TcdB_{10463}$ was incubated as described in Example 1 (C) with 100 µM IP6. Following the incubation, the smaller 63 kD fragment of toxin protein, split off by the protease activity, was separated off, by the batch being purified via microcon tubes (Millipore, exclusion size 100 kD). This 63 kDa fragment of $TcdB_{10463}$ was then examined for rounding of the cells in the CHO test according to Moos et al. (2000) described in Example 2. Here, the protein was added undiluted and in dilution stages to the cells.

In this experiment, it was found that the 63 kDa fragment, which has the glucosyltransferase function of $TcdB_{10463}$, under the given conditions alone is/was not able to bring about a cytotoxic effect. Neither in diluted nor in undiluted state a rounding of the cells (as a consequence of a glucosilation of specific GTpases of the Rho sub-family, which results in a blocking of signal transduction processes which results in a disaggregation of the cytoskeleton) could be observed. This finding that the toxin fragment generated by means of autocatalysis is inactive extracellularly, confirms the results of Pfeifer et al. (2003) and Rupnik et al (2005), which show that the split-off catalytic domain of $TcdB_{10463}$ is not taken up into eucaryontic cells and is therefore inactive in the cell medium. (Whereas in these papers, however, an autocatalytic activity of the LCTs is explicitly ruled out [Pfeifer et al., 2003] or there is speculation concerning a cellular protease for the activation of the LCTs [Rupnik et al., 2005], the experiment results obtained in connection with the present invention show for the first time that the N-terminal toxin fragment is split off autocatalytically).

The cytotoxic effect of $TcdB_{10463}$ and other LCTs can consequently be inhibited in that the proteolytic cleavage of the toxins is already induced before penetration of the toxins into the cells.

Example 4

Demonstration of the Active Centre of the Protease of TcdB

EPNP-inactivated (cf. Example 2) and untreated TcdB10463 were separated by means of SDS gel and represented by zinc stain. Then the bands corresponding to the proteins were cut out and divided into small pieces. These were removed of colour and dried, then reduced in 2 mM DTT and alkylated with 20 mM iodacetamide. After the washing and renewed drying of the gel fragments, these were digested with trypsin overnight at 37° C. The resulting peptides were then separated by HPLC (NanoAcquity ultraperformance liquid chromatography, Waters, Milford, USA). For this, 4.1.1 of the samples were applied onto a reverse-phase column (NanoEase BEH $C_{18}$ (75 μm×10 cm) of Waters, Milford, USA) in 2% mobile phase B buffer (0.1% formic acid in acetonitrile). Mobile phase A buffer contained 0.1% formic acid in $H_2O$. Then the fragments were eluted through a gradient of 3-40% mobile phase B buffer (90 min at 300 nl/min) from the column.

The eluted fragments were then examined by mass spectrometry. For this, a Q-Tof Premier mass spectrometer of the company Waters was used. The apparatus was calibrated with a [Glu-1]-fibrinogen peptide solution (500 fmol/μl at 300 nl/min) via the reference-sprayer of the NanoLockSpray source (Waters). For the analysis of the results, the MassLnyx4.1 software (Waters) was used.

Figure 3A:
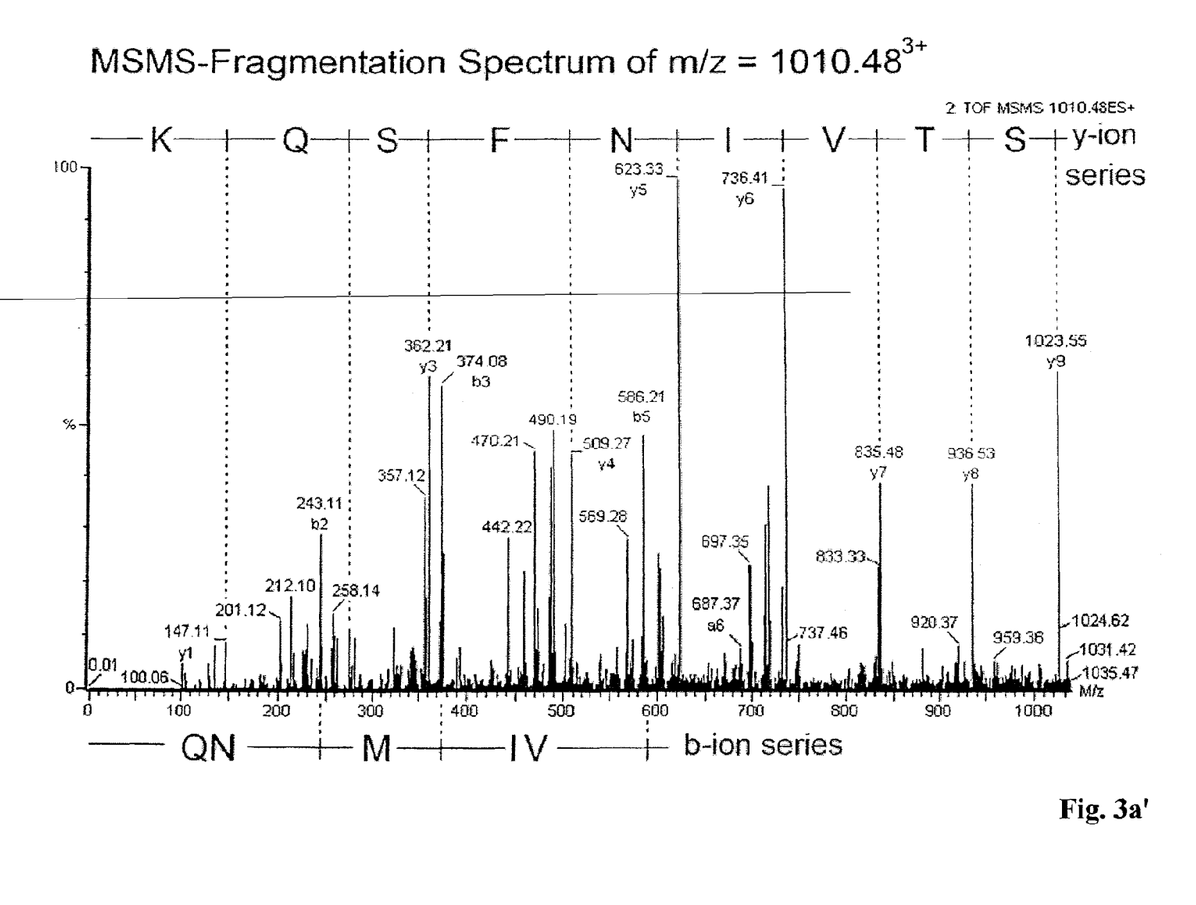
FIG. 3: ESI-LCMSMS analysis after tryptic digestion of the native (a) and of the EPNP-modified (b) TcdB protein. MS survey scanes (large image) and fragmentation spectra (insert).
Figure 3B:
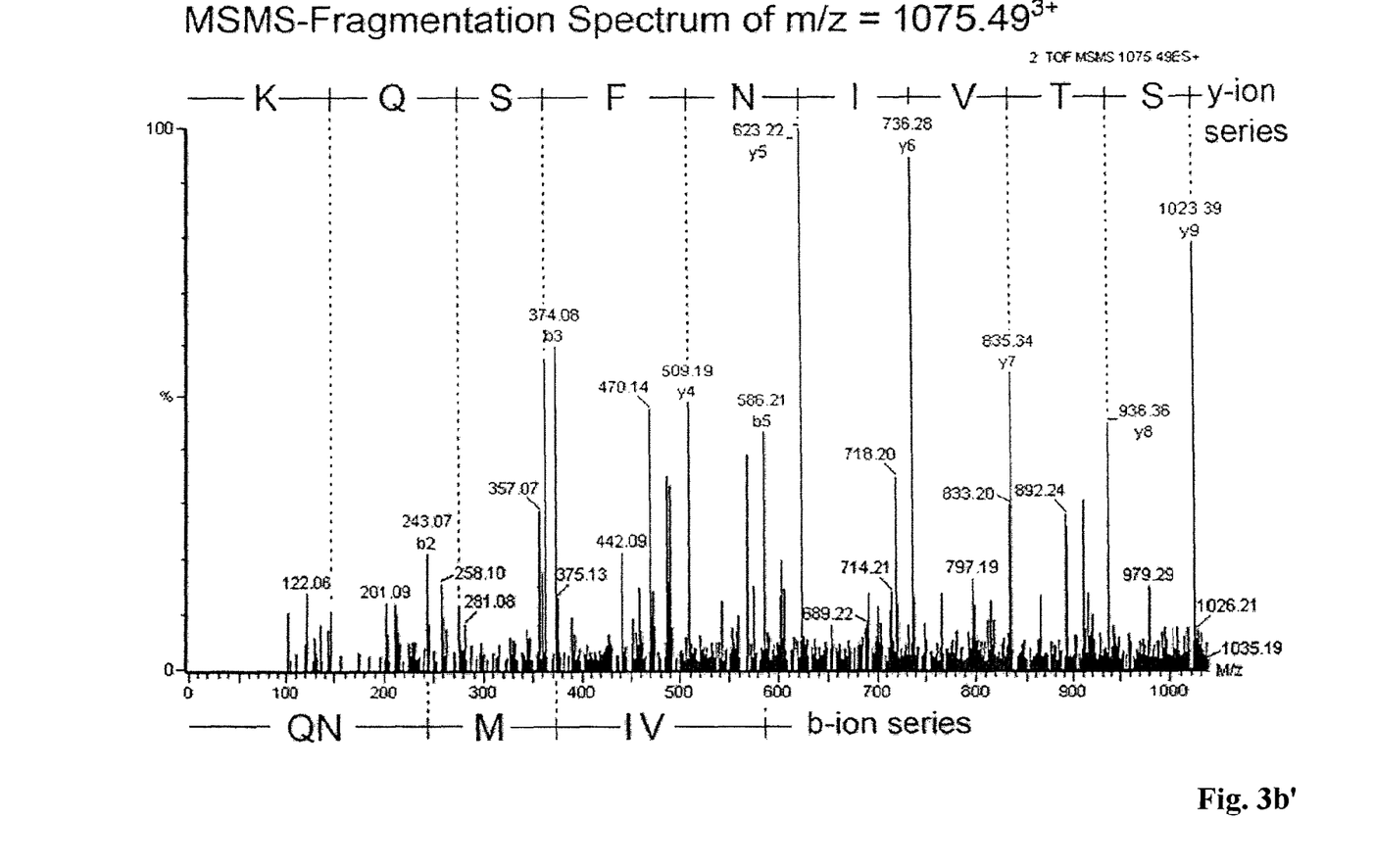

The analysis of the results shows that the untreated TcdB differs from the EPNP-treated toxin only in a tryptic fragment (Illustration 3). This fragment comprises the amino acids AS 1653 to 1678 of the TcdB protein according to TcdB amino acid sequence No. P18177 (SwissProt/TrEMBL) with the DXG motif at Position 1665, characteristic for aspartate proteases.

A comparison of the amino acid sequence AS 1653 to AS 1678 of the catalytic centre of TcdB with the corresponding catalytic centres and protein regions of the toxins TcdA, TcsL and Tcnα shows that the region is highly conserved (see Tab. 3).

The specialist in the art can therefore generate antibodies or other proteins by known methods, which interact specifically with the active centre of the protease domain of the toxins, and therefore for example can prevent the autocatalytic cleavage of the LCTs. Equally well, antibodies or proteins can be generated, which do not directly block the active centre, but rather are directed to adjacent regions and hence prevent the autoproteolytic cleavage of the toxin sterically.

Example 5

Inhibition of the TcdB Effect Through Antibodies as a Result of Immunisation with Inactivated TcdB In order to induce a protection against the cytotoxic effects of TcdB, the following TcdB preparations were produced and used for immunisation in rabbits:
Preparation A: TcdB, inactivated with formalin
Preparation B: TcdB, inactivated with EPNP (cf. Example 2)
Preparation C: TcdB fragment AS1601-1716 (DSG motif)
Preparation D: TcdB fragment AS1508-1601 (part of the inosine-binding motif)
Preparation E: TcdB fragments AS 1508-2157
(DSG motif and entire inosine-binding motif)

The TcdB fragments were expressed by methods known to the specialist in the art in the plasmid pET-19 (Novagen) and purified via the attached His tag. Then the His tag was split off by means of enterokinase digestion. The purity of the protein was checked in the SDS gel (data not shown).

For immunisation, rabbits were firstly initially immunised with the antigen and subsequently subjected to several booster immunisations. Finally, polyclonal antiserums were obtained from the blood of the rabbits.

In order to check the neutralising effect of the polyclonal antiserums, firstly TcdB was pre-treated with polyclonal antiserum (dilution stage 1:100) and incubated for 1 h at room temperature. Then the neutralising effect of the antiserums was checked as described in Example 2 with the aid of the CHO test. The measurement for the neutalising effect of the serums was how long the cells were protected from the cytotoxic effect of the TcdB.

The rabbits immunised with preparation A showed only a small antibody titer (cf. Tab. 4), in addition the serum of these rabbits did not have a neutralising effect. This finding corresponds to the results known to the specialist in the art of immunisation experiments with formalised LCTs.

The animals which were immunised with preparation B did indeed develop a distinct titer (dilutable up to 1:1500), however this antiserum also did not show any neutralising effect in the CHO test (Tab. 4).

The rabbits which had been immunised with the preparations C to E likewise showed an antibody titer, and in addition their polyclonal serums showed a distinctly neutralising effect in the CHO test (Tab. 4). The polyclonal serum which was generated by immunisation with preparation E showed the best neutralising characteristics here.

The serums which were produced by separate immunisation with the preparations C and D showed a smaller neutralising effect, compared with this.

The success of the immunisation with fragment D, which comprises a part of the inositol-binding region, proves that this section of the LCTs is an important region for the activation of the toxins. The binding of the IP6 in this toxin section leads to the activation of the autocatalytic protease activity and hence also to the activation of the LCTs.

The neutralising effect of the region around the DSG motif proves that antibodies which are directed against the active centre of the protease can inhibit the proteolytic activity. With such antibodies, therefore, a protection from the toxic effects of the LCTs can also be achieved in vivo.

With the immunisation with preparation E, only the two fragments of the successful preparations C and D were used together. The success of the immunisation with both TcdB fragments is based on the fact that in the animals antibodies are induced which are directed towards the active centre of the protease and also those antibodies which bind to the inositol phosphate-binding region. The effect of the antiserum is therefore based on the fact that for the first time specific antibodies were able to be induced, which systematically prevent the activation of the toxin.

The autocatalytic cleavage of the toxins is important for the natural uptake of the LTCs into their target cells, because only thus is the N-terminal fragment released, imparting the actual toxic activity, in the target cells. The binding of specific antibodies in the environment of the DSG motif of the aspartate protease and the inositol phosphate binding site prevents the autocatalytic cleavage of the toxins. In patients, therefore, through the use of toxin fragments, which are necessary for the autocatalytic cleavage of the LCTs, an effective immunisation against LCTs can be achieved.

LITERATURE

Ausubel, F. M. et al.: "Current Protocols in Molecular Biology" (2003), John Wiley and Sons. Inc.
Rupnik et al. (2005) "Characterization of the cleavage site and function of resulting cleavage fragments after limited proteolysis of *Clostridium difficile* toxin B(TcdB) by host cells." *Mikrobiol* 151, 199-208.
Moos et al. (2000) "Purification and evaluation of large clostridial cytotoxins that inhibit small GTPases of Rho and Ras subfamilies" Meth Enzymol. 325: 114-125.
Pfeifer et al. (2003) "Cellular Uptake of *Clostridium difficile* toxins B" J. Biol. Chem. 278: 44535-41.

Rao et al. (1998) "Molecular and biotechnological aspects of microbial proteases" Microbiol. Mol. Biol. Rev. 62: 597-635.
Salto et al. (1994) "In vitro characterization of nonpeptide irreversible inhibitors of HIV proteases", J. Biol. Chem. 269: 10691-8.
Tang (1971) "Specific and irreversible inactivation of pepsin by substrate-like Epoxides", J. Biol. Chem. 246: 4510-17.

TABLE 1

Autocatalytic cleavage of TcdB$_{10463}$ with the addition of defined inositol phosphates

| IP | 1 mM | 100 µM | 10 µM |
|---|---|---|---|
| 1, 5 | − | − | − |
| 1, 4 | − | − | − |
| 4, 5 | − | − | − |
| 1, 4, 5 | − | − | − |
| 2, 3, 5 | − | − | − |
| 1, 3, 5 | − | − | − |
| 1, 3, 5, 6 | − | − | − |
| 1, 2, 3, 4, 6 | − | − | − |
| 1, 3, 4 | + | − | − |
| 1, 3, 4, 5 | + | − | − |
| 3, 4, 6 | + | − | − |
| 1, 2, 3, 4 | + | − | − |
| 1, 2, 3, 4, 5 | + | − | − |
| 1, 2, 3, 5, 6 | + | + | − |
| 1, 3, 4, 5, 6 | + | + | − |
| 3, 4, 5, 6 | + | + | − |
| 2, 3, 4, 5, 6 | + | + | − |
| 1, 4, 5, 6 | + | + | − |
| 1, 2, 3, 4, 5, 6 | + | + | + |

TABLE 2

Cell rounding (in %) of CHO cells after incubation with TcdB$_{10463}$ - with or without EPNP pre-treatment

| Dilution | Rounded cells [%] after 3 h | |
|---|---|---|
| | TcdB-10463 | TcdB-10463 + EPNP |
| $10^{-3}$ | 100% | 100% |
| $10^{-4}$ | 100% | 100% |
| $10^{-5}$ | 100% | 50% |
| $10^{-6}$ | 100% | 10% |
| $10^{-7}$ | 10% | <5% |
| $10^{-8}$ | <5% | <5% |

TABLE 3

Comparison of the amino acid sequence AS 1653 to AS 1678 of the catalytic centre of the protease function of TcdB with the corresponding catalytic centres and protein regions of the toxins TcdA, TcsL and Tcnα

| Toxin | Homologous Sequence Range |
|---|---|
| TcdB-10463 | 1653-QNMIVEPNYDLDDSGDISSTVINFSQ-1678 [SEQ ID NO: 1] |
| TcdA-10463 | 1651-RNVVVEPIYNPDTGEDISTSL-DFSY-1675 [SEQ ID NO: 2] |
| TcsL | 1654-QNLIVEPSYHLDDSGNISSIVINFSQ-1679 [SEQ ID NO: 3] |
| Tcnα | 1641-CNVIVSGSNKLNSEGDLADT-IDVLD-1665 [SEQ ID NO: 4] |

TABLE 4

Start of cell rounding (in h) of CHO cells after incubation with TcdB, which was pre-treated with polyclonal antiserum.

| Preparation | Antibody Titer | Start of cell rounding after |
|---|---|---|
| A | 1:100 | 1.5 h |
| B | 1:1500 | 3 h |
| C | 1:750 | 12-15 h |
| D | 1:500 | 9-12 h |
| E | 1:1000 | >24 h |

The invention claimed is:

1. Method for treating a patient suffering from *clostridium* infection, comprising:

selecting one or more activators of an autocatalytic protease activity of LCTs (=large clostridial cytotoxin) that interact with one or more protease of *Clostridium difficile* toxin A (TcdA), *Clostridium difficile* toxin B (TcdB), *Clostridium sordellii* lethal toxin (TcsL) or *Clostridium novyi* α-toxin Tcn(α) and that initiate a protease activity of said one or more protease, based on detecting the splitting off of an N-terminal fragment of the LCT, administering to said patient a medicament comprising said one or more activators, wherein the one or more activators are administered in an amount effective to activate and bring about the autocatalytic cleavage of said LCTs in the patient's gut outside a cell of the patient, wherein the protease activity of said one or more protease is initiated and wherein a cytotoxically effective fragment of said *Clostridium difficile* toxin A (TcdA), *Clostridium difficile* toxin B (TcdB), *Clostridium sordellii* lethal toxin (TcsL) or *Clostridium novyi* α-toxin (Tcnα), respectively, is auto catalytically split off via said protease activity in the patient's gut outside the cell of the patient.

2. The method according to claim 1, wherein the active ingredient is one activator and the activator is an inositol phosphate.

3. The method according to claim 2, wherein the inositol phosphate is inositol hexaphosphate (IP6).

4. The method according to claim 1, wherein the active ingredient is one activator and the activator is a IP6 analogous and activates the autocatalytic protease activity of the LCTs.

5. The method for treating a patient suffering from *clostridium* infection of claim 1 wherein said administering further comprises administering one or more antigen active ingredient selected from the group consisting of a TcdB protein fragment which comprises at least a DXG motif at position 1665 of SEQ ID NO 1 a TcdB protein fragment which comprises the-amino acid sequence of positions 1653 to 1678 of SEQ ID NO 1, a TcdA protein fragment which comprises at least a DXG motif at position 1662 of SEQ ID NO: 2, a TcdA protein fragment which comprises the amino acid sequence of amino acid positions 1651 to 1675 of SEQ ID NO: 2, a TcsL protein fragment which comprises at least a DXG motif at position 1666 of SEQ ID NO 3, a TcsL protein fragment which comprises the amino acid sequence of amino acid positions 1654 to 1679 of SEQ ID NO: 3, and a Tcnα protein fragment which comprises at least the amino acid sequence of positions 1641 to 1665 of SEQ ID NO: 4.

6. The method according to claim 1, wherein said medicament comprises an active ingredient and said active ingredient consists of said one or more activators.

7. The method of claim 1, wherein the cytotoxically effective fragment is an N-terminal toxin fragment of the LCT and is detectable.

8. The method of claim 7, further comprising detecting the N-terminal toxin fragment.

9. The method of claim 6, wherein the active ingredient is one activator.

10. The method of claim 1, wherein the one or more activators relieves LCT poisoning.

* * * * *